(12) United States Patent
Okada et al.

(10) Patent No.: US 8,084,650 B2
(45) Date of Patent: Dec. 27, 2011

(54) ADAMANTANE DERIVATIVE, RESIN COMPOSITION CONTAINING SAME, AND OPTOELECTRONIC MEMBER AND SEALING AGENT FOR ELECTRONIC CIRCUIT USING THOSE

(75) Inventors: Yasunari Okada, Chiba (JP); Hajime Ito, Chiba (JP); Hideki Yamane, Chiba (JP); Nobuaki Matsumoto, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 496 days.

(21) Appl. No.: 12/160,534

(22) PCT Filed: Jan. 19, 2007

(86) PCT No.: PCT/JP2007/050795
§ 371 (c)(1),
(2), (4) Date: Jul. 10, 2008

(87) PCT Pub. No.: WO2007/086324
PCT Pub. Date: Aug. 2, 2007

(65) Prior Publication Data
US 2010/0298491 A1   Nov. 25, 2010

(30) Foreign Application Priority Data

Jan. 27, 2006 (JP) .................. 2006-019729

(51) Int. Cl.
*C07C 39/17* (2006.01)
*C08L 63/00* (2006.01)
*B32B 27/38* (2006.01)

(52) U.S. Cl. ....... 568/732; 523/403; 549/517; 428/1.53; 428/413

(58) Field of Classification Search .................. 523/403; 549/517; 568/732; 428/1.53, 413
See application file for complete search history.

(56) References Cited

U.S. PATENT DOCUMENTS

| | | | | |
|---|---|---|---|---|
| 3,795,658 A | * | 3/1974 | Thompson et al. | 528/97 |
| 3,821,275 A | * | 6/1974 | Inamoto et al. | 558/429 |
| 6,066,711 A | | 5/2000 | Hanazawa et al. | |
| 6,429,314 B1 | * | 8/2002 | Ishii et al. | 546/112 |
| 6,720,460 B2 | * | 4/2004 | Yoshikawa et al. | 568/719 |
| 7,378,461 B2 | * | 5/2008 | Haraguchi et al. | 523/445 |

FOREIGN PATENT DOCUMENTS

| | | |
|---|---|---|
| JP | 4 39665 | 2/1992 |
| JP | 6 128360 | 5/1994 |
| JP | 6 305044 | 11/1994 |
| JP | 7 278260 | 10/1995 |
| JP | 9 302077 | 11/1997 |
| JP | 10 130371 | 5/1998 |
| JP | 10 219080 | 8/1998 |
| JP | 2003 321530 | 11/2003 |
| JP | 2005 146253 | 6/2005 |
| JP | 2005 232112 | 9/2005 |
| JP | 2006307063 A | * 11/2006 |
| SU | 593432 | * 3/1980 |
| SU | 593432 A | * 3/1980 |

OTHER PUBLICATIONS

Eastmond, G. C. et al., "Pendant adamantyl poly(ether imide)s: synthesis and a preliminary study of properties", European Polymer Journal, Pergamon, vol. 35, pp. 2097-2106, (1999).

* cited by examiner

*Primary Examiner* — Tae H Yoon
(74) *Attorney, Agent, or Firm* — Oblon, Spivak, McClelland, Maier & Neustadt, L.L.P.

(57) ABSTRACT

Disclosed is an adamantane derivative which provides a cured product excellent in optical characteristics such as transparency and light resistance, long-term heat resistance, electrical characteristics such as and dielectric constant, and low water absorption. Also disclosed are a resin composition containing the adamantane derivative, a sealing agent for electronic circuits, optical electronic member, semiconductor device and copper-clad laminate all using the resin composition, and a radiation-sensitive resin composition which contains the above-mentioned adamantane derivative as a crosslinking agent. Specifically disclosed are an adamantane derivative represented by the formula (I-1) below, a resin composition containing the adamantane derivative, a sealing agent for electronic circuits, optical electronic member, semiconductor device and copper-clad laminate, all using the resin composition, and a radiation-sensitive resin composition which contains the above-mentioned adamantane derivative as a crosslinking agent.

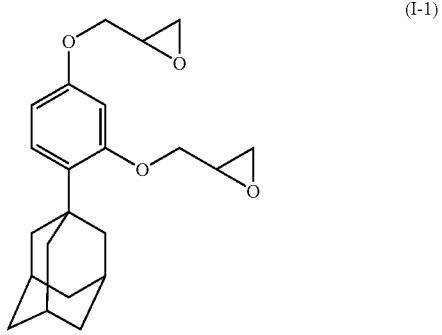

(I-1)

13 Claims, No Drawings

US 8,084,650 B2

ADAMANTANE DERIVATIVE, RESIN COMPOSITION CONTAINING SAME, AND OPTOELECTRONIC MEMBER AND SEALING AGENT FOR ELECTRONIC CIRCUIT USING THOSE

TECHNICAL FIELD

The present invention relates to a novel adamantane derivative giving a cured product having excellent optical characteristics such as transparency, light resistance and the like, long-term heat resistance, excellent electric characteristics such as dielectric constant and the like, and low water absorption; and an optical electronic member, a sealing agent for an electronic circuit, and the like using it. More particularly, it relates to an adamantane derivative giving a cured product having excellent optical characteristics such as transparency, light resistance and the like, long-term heat resistance, excellent electric characteristics such as dielectric constant and the like, and low water absorption, useful as a sealing agent for an electronic circuit (a sealing agent for an optical semiconductor, an organic electroluminescent (EL) device and the like), an optical electronic member (an optical waveguide, an optical communication lens, an optical film and the like) and an adhesive agent for them, or a crosslinking agent for a radiation-sensitive resin composition, and others; a resin composition containing it; a sealing agent for an electronic circuit, an optical electronic member, an semiconductor device, and a copper-clad laminate all using the resin composition thereof; and a radiation-sensitive resin composition containing the above-mentioned adamantane derivative as a crosslinking agent.

BACKGROUND ART

An adamantane contains 4 cyclohexane rings condensed to form a cage skeleton, and is a highly symmetric and stable compound. Its derivatives show specific performances, thus are known to be useful as raw materials for a pharmaceutical raw material, a high performance industrial material and the like. An adamantane has, for example, optical characteristics, heat resistance and the like, and therefore attempts have been made to use it for an optical disk substrate, an optical fiber, a lens and the like (for example, refer to Patent Documents 1 and 2). Further, there have been attempts to use an adamantane ester as a raw material of resin for a photoresist by utilizing its acid-sensitive property, dry etching resistance, UV light transparency and the like (for example, refer to Patent Document 3).

In recent years, in order to achieve higher performance or improvement of an optical/electronic component, studies are progressing for higher precision, wider viewing angle, and enhanced image quality of a flat panel display using a liquid crystal, an organic EL device and the like, for higher intensity/shorter wavelength and whitening of a light source using such optical semiconductors as a light emitting diode (LED) and the like, and further for higher frequency of an electronic circuit and for an optical circuit/communication, and others.

As a method for the improvement, basic materials such as a liquid crystal material, a light emitting material for an organic EL device, and the like have been investigated and developed. The investigation has also been done to seek higher performance of a resin that is used along with those materials as a coating material, a sealant and the like. As a resin for a coating material of an optical/electronic component and for a sealant, many kinds of thermosetting resin, light-curable resin, or thermoplastic resin have been applied. They have been applied in accordance with their respective characteristics in heat resistance, transparency, solubility, adhesiveness, and others of each resin.

In the field of LED, which is advanced in terms of high performance, an illumination, a light and the like using a white LED comprising light emitting devices of near ultra violet and blue lights have been proposed and developed for practical use. In addition, it is expected that they will be developed to be used for a home lighting and an automobile in the future. An LED device is sealed by a resin containing a fluorescent material in an inorganic semiconductor. For such applications, thermosetting resins such as conventional bisphenol A epoxy resin and the like have limitation in heat resistance and light resistance, thus a sealant fulfilling those required characteristics is desired (for instance, refer to Non-Patent Document 1).

Furthermore, in the display field, an organic EL device of small size, high precision, and energy saving is used, and such type as top-emission is employed. Accordingly, a sealing resin itself is required, for the use in an organic EL device, to have further improved transparency, light resistance, heat-resistance, mechanical strength and others in addition to functions such as gas barrier, adhesion of conventional sealing boards such as stainless steel and the like to a glass substrate, and others (for instance, refer to Non-Patent Document 2).

When manufacturing a liquid crystal display, an attempt has been made to form a permanent film such as an interlayer insulation film, a protection film for a color filter and the like by a radiation-sensitive resin composition (refer to Patent Document 5, for example). In order to form such a permanent film for a liquid crystal display, a radiation-sensitive resin composition having excellent transparency in addition to heat resistance and solvent resistance is required. However, it cannot be said that a conventional radiation-sensitive resin composition fully satisfies heat resistance and transparency.

Moreover, in an electronic circuit integrated with a semiconductor and the like, as a computerized society progresses, the increase in volume of information and communication speed and the miniaturization of a device have been progressing. A resin-sealing type semiconductor device (a semiconductor package) is in the direction of higher density, integration, speed of movement and the like of the device, thus a semiconductor device of further miniaturized and thinned than conventional packages (QFP (quad flat package) and the like) is required. For such requirement, there is a semiconductor device enabling high-density mounting such as BGA (ball grid array), CSP (chip size package), and a bear chip mounting. As examples of electric appliances using such a semiconductor device, there may be mentioned a digital camera, a video deck, a note-type personal computer, a mobile phone, and the like, and as these product themselves progress toward more miniature, slim, and complex, they are required higher impact resistance and reliability, and so are their internal substrates and electronic members. In addition, as lead contained in a usual solder (a Sn—Pb type) cannot be used due to an environmental regulation, an alternative material (a Sn—Ag—Cu type, a Sn—Ag—Cu—Bi type, a Sn—Zn—Bi type, a Sn—Cu type) needs to be used. Since these alternative materials have higher melting points, heat resistance endurable to it has been required. A copper-clad laminate used for these semiconductor devices, which is composed of a copper foil and a prepreg obtained by impregnating/drying a glass cloth with an epoxy resin and the like, is required by the same token solder heat resistance and also not to contain water that causes decrease of heat resistance and reliability.

Furthermore, an optical circuit using an optical waveguide and the like that enables further high speed processing has also been investigated. When conventionally used resins such as a bisphenol A epoxy resin and the like are used as a resin for a sealing resin in these uses, an adhesive resin and a film, or a resin for a lens, there have been such problems as high dielectric constant and insufficient heat resistance in an electronic circuit. There have also been problems of a decrease in transparency, or yellowing and the like due to resin deterioration in an optical waveguide and an LED sealant, and others. For instance, in Patent Document 6, a sealant resin composition using a bisphenol A epoxy resin is disclosed, but it cannot be said that this has sufficient heat resistance. In Patent Documents 7 and 8, a resin composition using an alicyclic epoxy resin such as 3',4'-epoxycyclohexylmethyl-3,4-epoxycyclohexanecarboxylate is disclosed, but it has a problem of high water absorption though its cured product has high heat resistance.

Patent Document 1: Japanese Patent Laid-Open Publication No. H6-305044
Patent Document 2: Japanese Patent Laid-Open Publication No. H9-302077
Patent Document 3: Japanese Patent Laid-Open Publication No. H4-39665
Non-Patent Document 1: Monthly "Material Stage" June 2003, pp. 20-24, published by Technical Information Institute Co., Ltd.
Non-Patent Document 2: Monthly "Material Stage" March 2003, pp. 52-64, published by Technical Information Institute Co., Ltd.
Patent Document 5: Japanese Patent Laid-Open Publication No. 2005-232112
Patent Document 6: Japanese Patent Laid-Open Publication No. H10-219080
Patent Document 7: Japanese Patent Laid-Open Publication No. H6-128360
Patent Document 8: Japanese Patent Laid-Open Publication No. H7-278260

DISCLOSURE OF THE INVENTION

Problems to be Solved by the Invention

In view of the above-mentioned circumstances, an object of the present invention is to provide an adamantane derivative giving a cured product having excellent optical characteristics such as transparency, light resistance and the like long-term heat resistance, excellent electric characteristics such as dielectric constant, and low water absorption, suitable for a sealing agent for an electronic circuit (a sealing agent for an optical semiconductor, an organic EL device and the like), an optical electronic member (an optical waveguide, an optical communication lens, an optical film and the like) and an adhesive agent for them, a crosslinking agent for a radiation-sensitive resin composition, and others; a resin composition containing it; a sealing agent for an electronic circuit, an optical electronic member, a semiconductor device and a copper-clad laminate all using the resin composition thereof; and a radiation-sensitive resin composition containing the above-mentioned adamantane derivative as a crosslinking agent.

Means for Solving the Problems

The present inventors carried out extensive investigation, and as a result, have found that a resin composition giving a cured product suitable as an optical electronic member and the like could be obtained by using a specific adamantane derivative. Namely, it was found that a cured product having excellent heat resistance, transparency, electric characteristics such as low dielectric constant and the like, and low water-absorption could be obtained by curing a resin composition comprising an epoxy curing agent and a glycidyl ether of a certain adamantane derivative containing a phenolic hydroxyl group. By this, it was further found that the above-mentioned resin composition which is excellent in transparency, heat resistance, and electric characteristics such as low dielectric constant and the like could be used as a sealing agent, an adhesive agent, a coating agent and the like with improved transparency, light resistance, heat resistance, electric characteristics, and low water-absorption. The present invention was accomplished based on these findings.

Namely, the present invention provides a following adamantane derivative; a resin composition containing it; a sealing agent for an electronic circuit, an optical electronic member, an semiconductor device and a copper-clad laminate all using the resin composition thereof; and a radiation-sensitive resin composition containing the above-mentioned adamantane derivative as a crosslinking agent.

1. An adamantane derivative represented by the following general formula (I-1).

[Formula 1]

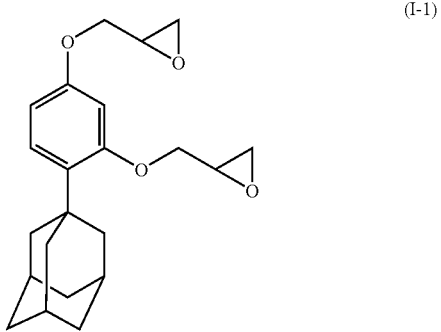

(I-1)

2. An adamantane derivative represented by the following general formula (I-2).

[Formula 2]

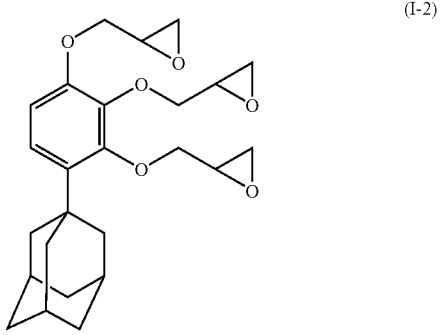

(I-2)

3. An adamantane derivative represented by the following general formula (I-3).

[Formula 3]

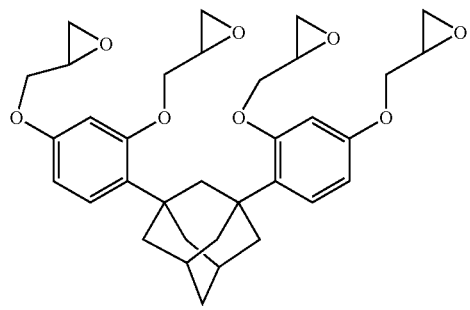
(I-3)

4. An adamantane derivative represented by the following general formula (I-4).

[Formula 4]

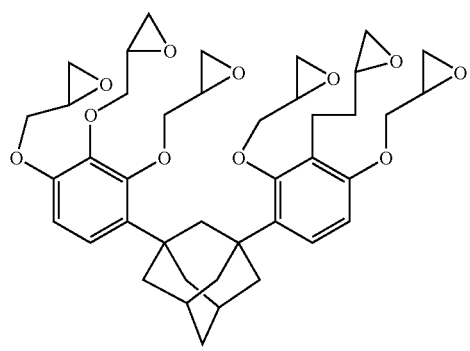
(I-4)

5. An adamantane derivative represented by the following general formula (I-5).

[Formula 5]

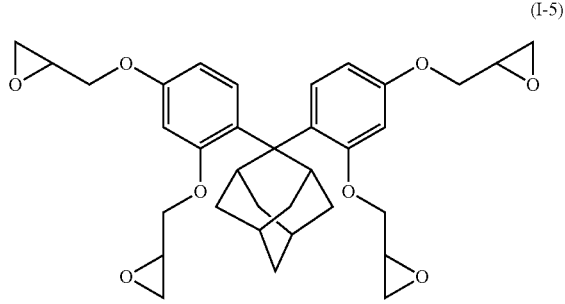
(I-5)

6. An adamantane derivative represented by the following general formula (II-1).

[Formula 6]

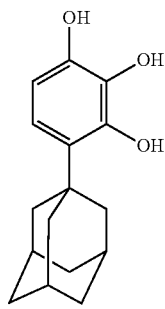
(II-1)

7. An adamantane derivative represented by the following general formula (II-2).

[Formula 7]

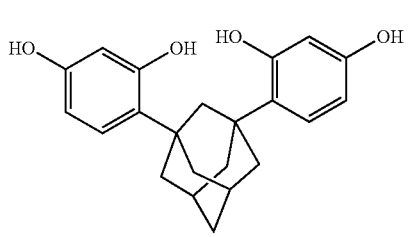
(II-2)

8. An adamantane derivative represented by the following general formula (II-3).

[Formula 8]

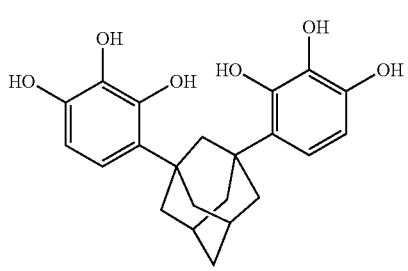
(II-3)

9. An adamantane derivative represented by the following general formula (II-4).

[Formula 9]

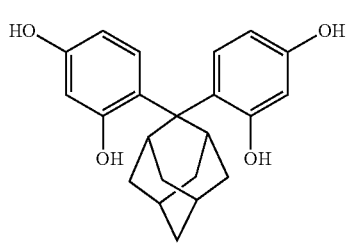
(II-4)

10. A method of producing an adamantane derivative represented by the following general formula (I) by allowing an adamantane derivative represented by the following general formula (II) to react with epichlorohydrin.

[Formula 10]

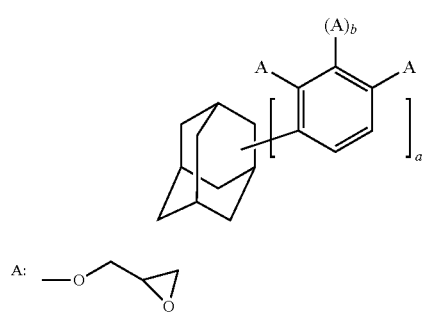

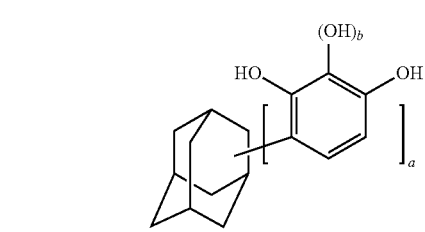

(In the formula, a is 1 or 2, and b is 0 or 1.)

11. A resin composition comprising (A) a resin containing the adamantane derivative according to any of the above 1 to 5 and (B) an epoxy resin curing agent.
12. The resin composition according to the above 11, wherein (B) the epoxy resin curing agent is one or more selected from a cationic polymerization initiator, an acid anhydride compound, and a phenolic resin.
13. The resin composition according to the above 11 or 12, wherein it further contains (C) a curing accelerator and (D) an inorganic filler.
14. The resin composition according to the above 13, wherein it further contains (E) a flame retardant.
15. The resin composition according to any of the above 11 to 14, wherein it is used for sealing a semiconductor.
16. A radiation-sensitive resin composition containing the adamantane derivative according to any of the above 1 to 5 as a crosslinking agent.
17. An optical electronic member using the adamantane derivative according to any of the above 1 to 5 or the resin composition according to any of the above 11 to 14.
18. A sealing agent for an electronic circuit using the adamantane derivative according to any of the above 1 to 5 or the resin composition according to any of the above 11 to 14.
19. A semiconductor device wherein a semiconductor element is sealed by using the resin composition according to the above 15.
20. A copper-clad laminate produced by using the resin composition according to the above 15.

EFFECTS OF THE INVENTION

An adamantane derivative of the present invention or a resin composition containing the adamantane derivative gives a cured product having excellent optical characteristics such as transparency, light resistance and the like, long-term heat resistance, excellent electric characteristics such as dielectric constant and the like, and low water absorption, suitable for a sealing agent for an electronic circuit (a sealing agent for an optical semiconductor, an organic electroluminescent (EL) device, and the like), an optical electronic member (an optical waveguide, an optical communication lens, an optical film and the like) and an adhesive agent for them, a sealing agent for a semiconductor, a copper-clad laminate and the like. In addition, an adamantane derivative of the present invention is useful as a crosslinking agent for a radiation-sensitive resin composition used for a liquid crystal display and the like because of its excellent heat resistance and transparency.

BEST MODE FOR CARRYING OUT THE INVENTION

An adamantane derivative of the present invention is represented by the following general formulas (I-1) to (I-5) and (II-1) to (II-4).

[Formula 11]

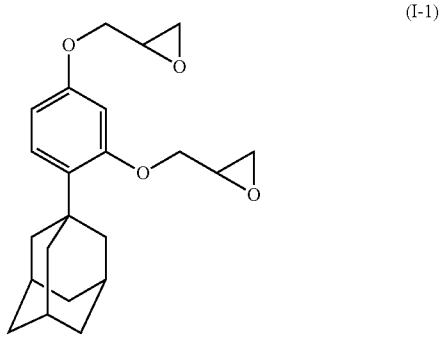

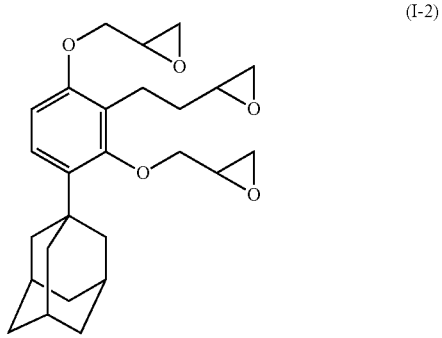

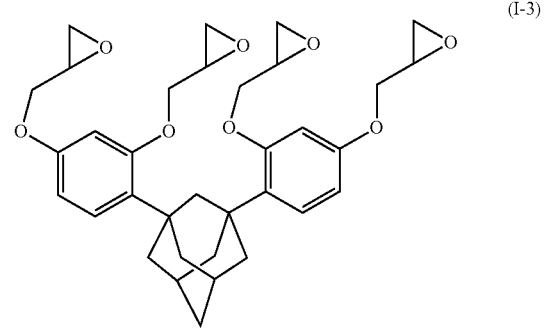

(I-4)
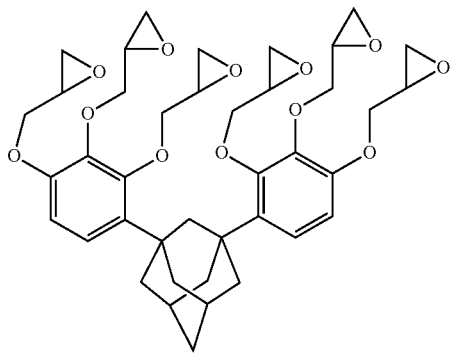

(I-5)
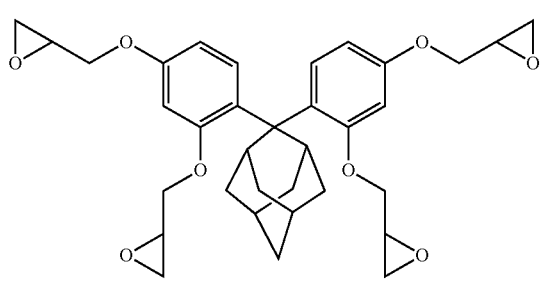

(II-1)
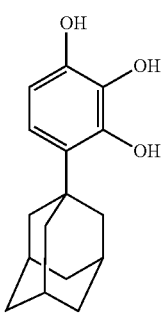

(II-2)
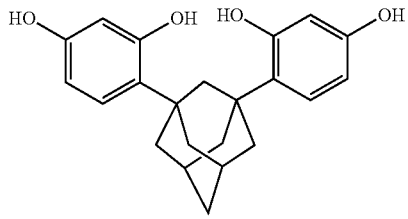

(II-3)
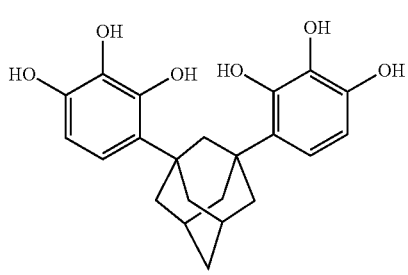

(II-4)
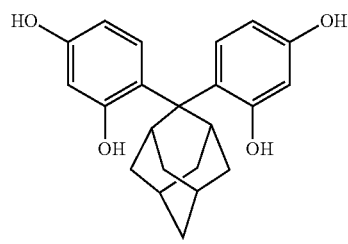

The adamantane derivatives represented by the above general formulas are 1-(2,4-diglycidyloxyphenyl)adamantane [the above general formula (I-1)], 1-(2,3,4-triglycidyloxyphenyl)adamantane [the above general formula (I-2)], 1,3-bis(2,4-diglycidyloxyphenyl)adamantane [the above general formula (I-3)], 1,3-bis(2,3,4-triglycidyloxyphenyl)adamantane [the above general formula (I-4)], 2,2-bis(2,4-digylcidyloxyphenyl)adamantane [the above general formula (I-5)], 1-(2,3,4-trihydroxyphenyl)adamantane [the above general formula (II-1)], 1,3-bis(2,4-dihydroxyphenyl)adamantane [the above general formula (II-2)], 1,3-bis(2,3,4-trihydroxyphenyl)adamantane [the above general formula (II-3)], and 2,2-bis(2,4-dihydroxyphenyl)adamantane [the above general formula (II-4)].

The adamantanes represented by the above general formulas (I-1) to (I-5), namely a glycidyloxy-containing adamantane derivative represented by the following general formula (I) can be produced by allowing a phenolic hydroxyl-containing adamantane derivative represented by the following general formula (II) to react with epichlorohydrin.

[Formula 12]

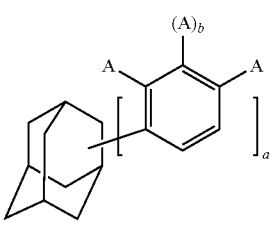
(I)

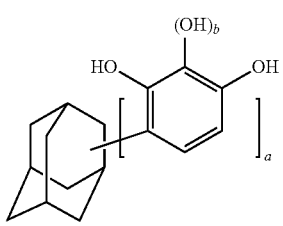
(II)

(In the formula, a is 1 or 2, and b is 0 or 1.)

Further, a glycidyloxy-containing adamantane derivative other than the adamantane derivative represented by the above general formula (I) can also be produced by allowing a corresponding phenolic hydroxyl-containing adamantane derivative to react with epichlorohydrin.

A phenolic hydroxyl-containing adamantane derivative represented by the above general formula (II) can be synthesized by allowing an adamantane to react with a polyvalent phenol in the presence of an acid catalyst. This synthesis process is designated as the first process. In addition, a phenolic hydroxyl-containing adamantane derivative other than the adamantane derivative represented by the above general formula (II) can be synthesized in a similar manner by using a corresponding adamantane as a raw material.

Examples of the above adamantanes include 1-adamantanol, 1-bromoadamantane, 1,3-adamantanediol, 1,3-dibromoadamantane, 1,3,5-adamantanetriol, 1,3,5-tribromoadamantane, 1,3,5,7-adamantanetetraol, 1,3,5,7-tetrabromoadamantane, 2-adamantanone, 4-hydroxy-2-adamantanone, 5-hydroxy-2-adamantanone and the like.

Specific examples of the phenolic hydroxyl-containing adamantane derivatives include 1-(2,4-dihydroxyphenyl)adamantane, 1-(2,3-dihydroxyphenyl)adamantane, 1-(2,5-dihydroxyphenyl)adamantane, 1-(2,6-dihydroxyphenyl)adamantane, 1-(3,4-dihydroxyphenyl)adamantane, 1-(2,3,4-trihydroxyphenyl)adamantane, 1-(2,4,5-trihydroxyphenyl)adamantane, 1-(2,4,6-trihydroxyphenyl)adamantane, 1,3-bis(2,4-dihydroxyphenyl)adamantane, 1,3-bis(2,3-dihydroxyphenyl)adamantane, 1,3-bis(2,5-dihydroxyphenyl)adamantane, 1,3-bis(2,6-dihydroxyphenyl)adamantane, 1,3-bis(3,4-dihydroxyphenyl)adamantane, 1,3-bis(2,3,4-trihydroxyphenyl)adamantane, 1,3-bis(2,4,5-trihydroxyphenyl)adamantane, 1,3-bis(2,4,6-trihydroxyphenyl)adamantane, 1,3-bis(2,3,5-trihydroxyphenyl)adamantane, 1,3-bis(2,3,6-trihydroxyphenyl)adamantane, 2,2-bis(2,4-dihydroxyphenyl)adamantane, 2,2-bis(2,3-dihydroxyphenyl)adamantane, 2,2-bis(2,5-dihydroxyphenyl)adamantane, 2,2-bis(2,6-dihydroxyphenyl)adamantane, 2,2-bis(3,4-dihydroxyphenyl)adamantane, 2,2-bis(2,3,4-trihydroxyphenyl)adamantane, 2,2-bis(2,4,5-trihydroxyphenyl)adamantane, 2,2-bis(2,4,6-trihydroxyphenyl)adamantane, 2,2-bis(2,3,5-trihydroxyphenyl)adamantane, 2,2-bis(2,3,6-trihydroxyphenyl)adamantane, 1,3,5-tris(2,4-dihydroxyphenyl)adamantane, 1,3,5-tris(2,3-dihydroxyphenyl)adamantane, 1,3,5-tris(2,5-dihydroxyphenyl)adamantane, 1,3,5-tris(2,6-dihydroxyphenyl)adamantane, 1,3,5-tris(3,4-dihydroxyphenyl)adamantane, 1,3,5-tris(2,3,4-trihydroxyphenyl)adamantane, 1,3,5-tris(2,4,5-trihydroxyphenyl)adamantane, 1,3,5-tris(2,4,6-trihydroxyphenyl)adamantane, 1,3,5-tris(2,3,5-trihydroxyphenyl)adamantane, 1,3,5-tris(2,3,6-trihydroxyphenyl)adamantane, 1,3,5,7-tetrakis(2,4-dihydroxyphenyl)adamantane, 1,3,5,7-tetrakis(2,3-dihydroxyphenyl)adamantane, 1,3,5,7-tetrakis(2,5-dihydroxyphenyl)adamantane, 1,3,5,7-tetrakis(2,6-dihydroxyphenyl)adamantane, 1,3,5,7-tetrakis(3,4-dihydroxyphenyl)adamantane, 1,3,5,7-tetrakis(2,3,4-trihydroxyphenyl)adamantane, 1,3,5,7-tetrakis(2,4,5-trihydroxyphenyl)adamantane, 1,3,5,7-tetrakis(2,4,6-trihydroxyphenyl)adamantane, 1,3,5,7-tetrakis(2,3,5-trihydroxyphenyl)adamantane, 1,3,5,7-tetrakis(2,3,6-trihydroxyphenyl)adamantane, and the like.

Specific examples of the glycidyloxy-containing adamantane derivatives include 1-(2,4-diglycidyloxyphenyl)adamantane, 1-(2,3-diglycidyloxyphenyl)adamantane, 1-(2,5-diglycidyloxyphenyl)adamantane, 1-(2,6-diglycidyloxyphenyl)adamantane, 1-(3,4-diglycidyloxyphenyl)adamantane, 1-(2,3,4-triglycidyloxyphenyl)adamantane, 1-(2,4,5-triglycidyloxyphenyl)adamantane, 1-(2,4,6-triglycidyloxyphenyl)adamantane, 1-(2,3,5-triglycidyloxyphenyl)adamantane, 1-(2,3,6-triglycidyloxyphenyl)adamantane, 1,3-bis(2,4-diglycidyloxyphenyl)adamantane, 1,3-bis(2,3-diglycidyloxyphenyl)adamantane, 1,3-bis(2,5-diglycidyloxyphenyl)adamantane, 1,3-bis(2,6-diglycidyloxyphenyl)adamantane, 1,3-bis(3,4-diglycidyloxyphenyl)adamantane, 1,3-bis(2,3,4-triglycidyloxyphenyl)adamantane, 1,3-bis(2,4,5-triglycidyloxyphenyl)adamantane, 1,3-bis(2,4,6-triglycidyloxyphenyl)adamantane, 1,3-bis(2,3,5-triglycidyloxyphenyl)adamantane, 1,3-bis(2,3,6-triglycidyloxyphenyl)adamantane, 2,2-bis(2,4-diglycidyloxyphenyl)adamantane, 2,2-bis(2,3-diglycidyloxyphenyl)adamantane, 2,2-bis(2,5-diglycidyloxyphenyl)adamantane, 2,2-bis(2,6-diglycidyloxyphenyl)adamantane, 2,2-bis(3,4-diglycidyloxyphenyl)adamantane, 2,2-bis(2,3,4-triglycidyloxyphenyl)adamantane, 2,2-bis(2,4,5-triglycidyloxyphenyl)adamantane, 2,2-bis(2,4,6-triglycidyloxyphenyl)adamantane, 2,2-bis(2,3,5-triglycidyloxyphenyl)adamantane, 2,2-bis(2,3,6-triglycidyloxyphenyl)adamantane, 1,3,5-tris(2,4-diglycidyloxyphenyl)adamantane, 1,3,5-tris(2,3-diglycidyloxyphenyl)adamantane, 1,3,5-tris(2,5-diglycidyloxyphenyl)adamantane, 1,3,5-tris(2,6-diglycidyloxyphenyl)adamantane, 1,3,5-tris(3,4-diglycidyloxyphenyl)adamantane, 1,3,5-tris(2,3,4-triglycidyloxyphenyl)adamantane, 1,3,5-tris(2,4,5-triglycidyloxyphenyl)adamantane, 1,3,5-tris(2,4,6-triglycidyloxyphenyl)adamantane, 1,3,5-tris(2,3,5-triglycidyloxyphenyl)adamantane, 1,3,5-tris(2,3,6-triglycidyloxyphenyl)adamantane, 1,3,5,7-tetrakis(2,4-diglycidyloxyphenyl)adamantane, 1,3,5,7-tetrakis(2,3-diglycidyloxyphenyl)adamantane, 1,3,5,7-tetrakis(2,5-diglycidyloxyphenyl)adamantane, 1,3,5,7-tetrakis(2,6-diglycidyloxyphenyl)adamantane, 1,3,5,7-tetrakis(3,4-diglycidyloxyphenyl)adamantane, 1,3,5,7-tetrakis(2,3,4-triglycidyloxyphenyl)adamantane, 1,3,5,7-tetrakis(2,4,5-triglycidyloxyphenyl)adamantane, 1,3,5,7-tetrakis(2,4,6-triglycidyloxyphenyl)adamantane, 1,3,5,7-tetrakis(2,3,5-triglycidyloxyphenyl)adamantane, 1,3,5,7-tetrakis(2,3,6-triglycidyloxyphenyl)adamantane, and the like.

Examples of the above polyvalent phenols include resorcinol, catechol, hydroquinone, pyrogallol, 1,3,5-benzenetriol, hydroxyhydroquinone and the like. The amount of a polyvalent phenol to be used is usually about 1 to about 20 mol equivalents and preferably 1.5 to 10 mol equivalents relative to a functional group of the above mentioned adamantanes. When the use amount of the polyvalent phenol is 1 mol equivalent or more, the reaction time is not too long, thus suitable. When the use amount of the polyvalent phenol is 20 mol equivalent or less, the balance between obtained effects and the economy is appropriate.

Examples of acidic catalysts include hydrochloric acid, sulfuric acid, p-toluenesulfonic acid, thioacetic acid, f3-mercaptopropionic acid and the like. The amount of an acidic catalyst to be used is usually about 0.01 to about 1 mol equivalent and preferably 0.05 to 0.8 mol equivalent relative to a functional group of a raw material adamantane. When the use amount of the acidic catalyst is 0.01 mol equivalent or more, the reaction time is not too long, thus suitable. When the use amount of the acidic catalyst is 1 mol equivalent or less, the balance between obtained effects and the economy is appropriate.

During the reaction, a solvent may be used as appropriate. Specific examples of the solvents include hexane, heptane, toluene, DMF (dimethylformamide), DMAc (N,N-dimethylacetamide), DMSO (dimethyl sulfoxide), ethyl acetate, diethyl ether, tetrahydrofuran, dimethoxyethane, methanol, ethanol, isopropylalcohol and the like.

The reaction between an adamantane and a polyvalent phenol is usually carried out at about 0 to about 200° C., and preferably 50 to 150° C. When the reaction temperature is 0° C. or above, the reaction rate does not decrease and remains moderate, thus the reaction time is shortened. And, when the reaction temperature is 200° C. or below, coloring of a reaction product can be suppressed. Applied pressure at the reaction in terms of absolute pressure is about 0.01 to about 10 MPa, and preferably normal pressure to 1 MPa. When the reaction pressure is 10 MPa or less, special equipment is not necessary as the safety is secured, thus it is useful from an industrial viewpoint. The reaction time is usually about 1 minute to about 24 hours, and preferably 1 to 10 hours.

A glycidyloxy-containing adamantane derivative represented by the above general formulas (I-1) to (I-5) can be synthesized by the reaction between the above-obtained phenolic hydroxyl-containing adamantane derivative, namely, 1-(2,4-dihydroxyphenyl)adamantane and an adamantane derivative represented by the above general formulas (II-1) to (II-4), with epichlorohydrin. This synthesis process is designated as the second process. In addition, a glycidyloxy-containing adamantane derivative other than the above general formula (I) can also be synthesized similarly by using a corresponding phenolic hydroxyl-containing adamantane derivative as a raw material.

The use ratio of a phenolic hydroxyl-containing adamantane derivative and epichlorohydrin is about 1 to about 10 mol of epichlorohydrin relative to 1 mol of the hydroxyl group of the phenolic hydroxyl-containing adamantane derivative.

The reaction between a phenolic hydroxyl-containing adamantane derivative and epichlorohydrin is usually carried out at about 0 to about 200° C., and preferably 20 to 150° C. When the reaction temperature is 0° C. or above, the reaction rate does not decrease and remains moderate, thus the reaction time is shortened. When the reaction temperature is 200° C. or below, coloring of a reaction product can be suppressed. Applied pressure at the reaction in terms of absolute pressure is about 0.01 to about 10 MPa, and preferably normal pressure to 1 MPa. When the reaction pressure is 10 MPa or less, special equipment is not necessary as the safety is secured, thus it is useful from an industrial viewpoint. The reaction time is usually about 1 minute to about 24 hours, and preferably 1 to 10 hours.

The above reaction is carried out usually in the presence of a basic catalyst. Examples of the basic catalysts include sodium amide, triethylamine, tributylamine, trioctylamine, pyridine, N,N-dimethylaniline, 1,5-diazabicyclo[4.3.0]nonene-5 (DBN), 1,8-diazabicyclo[5.4.0]undecene-7 (DBU), tetramethylammonium chloride, tetraethylammonium chloride, sodium hydroxide, potassium hydroxide, sodium hydride, sodium phosphate, potassium phosphate, sodium carbonate, potassium carbonate, silver oxide, sodium methoxide, potassium t-butoxide and the like.

The use amount of such a basic catalyst is usually about 1 to about 10 mol and preferably 1 to 5 mol relative to 1 mol of the hydroxyl group of the phenolic hydroxyl-containing adamantane derivative to be used.

Into the above basic catalyst, quaternary ammonium salts such as tetramethylammonium chloride, tetraethylammonium bromide and the like may be added as a phase-transfer catalyst. The use ratio of such a quaternary ammonium salt is about 0.01 to about 20 mol % and preferably 0.1 to 10 mol % relative to the basic catalyst.

The reaction is carried out in the presence or absence of a solvent. It is advantageous to use a solvent having 0.5% by mass or more of solubility of the phenolic hydroxyl-containing adamantane derivative in it, preferably 5% by mass or more. The use amount of the solvent is such that the concentration of the above adamantane derivative in the solvent is 0.5% by mass or more and preferably 5% by mass or more. At this time, the above adamantane derivative may be in the state of suspension, but preferably in solution. Specific examples of the solvents include hexane, heptane, toluene, DMF (dimethylformamide), DMAc (N,N-dimethylacetamide), DMSO (dimethyl sulfoxide), ethyl acetate, diethyl ether, tetrahydrofuran, acetone, MEK (methyl ethyl ketone), MIBK (methyl isobutyl ketone) and the like. They may be used singly or in a combination of two or more kinds.

Usually, an oligomer component including dimer and higher is included in a compound containing a group having an epoxy ring, and thus an oligomer including dimer and higher of a glycidyloxy-containing adamantane derivative is formed in the above reaction. Although there is no problem even if these oligomers are present, purification such as distillation, crystallization, column separation and the like may be done as appropriate. The purification method may be selected in accordance with properties of a reaction product and the kind of impure substance.

In the second process as mentioned above, if formation of the glycidyloxy group in the glycidyloxy-containing adamantane derivative is incomplete, contents of the glycidyloxy group can be improved by a ring closure reaction using a base catalyst.

This ring closure reaction is carried out usually at about 20 to about 200° C., and preferably 30 to 150° C. Applied pressure at the reaction in terms of absolute pressure is about 0.01 to about 10 MPa, and preferably normal pressure to 1 MPa. When the reaction pressure is 10 MPa or less, special equipment is not necessary as the safety is secured, thus it is useful from an industrial viewpoint. The reaction time is usually about 1 minute to about 24 hours, and preferably 30 minutes to 10 hours.

Examples of the base catalysts include sodium hydroxide, potassium hydroxide, sodium phosphate, potassium phosphate, sodium carbonate, potassium carbonate, calcium hydroxide, magnesium hydroxide and the like.

The amount of the base catalyst is about 0.1 to about 20% by mass and preferably 1 to 10% by mass relative to the glycidyloxy-containing adamantane derivative synthesized in the second process as mentioned above. When the use amount of the base catalyst is 0.1% by mass or more, the reaction rate does not decrease and remains moderate, thus the reaction time is shortened. When the use amount of the base catalyst is 20% by mass or less, the balance between obtained effects and the economy is appropriate.

The reaction is carried out in the presence or absence of a solvent. It is advantageous to use a solvent having 0.5% by mass or more of solubility of the glycidyloxy-containing adamantane derivative synthesized by the above-mentioned second process therein, preferably 5% by mass or above. The use amount of the solvent is such that the concentration of the above adamantane derivative in the solvent is 0.5% by mass or more and preferably 5% by mass or more. At this time, the above adamantane derivative may be in the state of suspension, but preferably in solution. Specific examples of the solvents include hexane, heptane, toluene, DMF (dimethylformamide), DMAc (N,N-dimethylacetamide), DMSO (dimethyl sulfoxide), ethyl acetate, diethyl ether, tetrahydrofuran, acetone, MEK (methyl ethyl ketone), MIBK (methyl isobutyl ketone) and the like. They may be used singly or in a combination of two or more kinds.

A reaction product may be purified by distillation, crystallization, column separation and the like, and a purification method may be selected in accordance with properties of a reaction product and the kind of impure substance.

A resin composition of the present invention contains (A) a resin containing the above glycidyloxy-containing adamantane derivative and (B) an epoxy resin curing agent. A resin composition of the present invention may be the one containing only the above glycidyloxy-containing adamantane derivative as the resin, or a resin mixture of the above glycidyloxy-containing adamantane derivative and a publicly known epoxy resin may be used in view of the optimization of mechanical strength of its cured product, solubility of the resin composition, workability and the like.

Examples of the publicly known epoxy resins include a bisphenol A epoxy resin, a bisphenol F epoxy resin, bisphenol S epoxy resin (bisphenol A diglycidyl ether, bisphenol AD diglycidyl ether, bisphenol S diglycidyl ether, bisphenol F diglycidyl ether, bisphenol G diglycidyl ether, tetramethyl-bisphenol A diglycidyl ether, bisphenol hexafluoroacetone diglycidyl ether, bisphenol C diglycidyl ether and the like), novolak epoxy resins such as a phenol novolak epoxy resin, a cresol novolak epoxy resin and the like, an alicyclic epoxy resin, nitrogen-containing cyclic epoxy resins such as triglycidyl isocyanurate, a hydantoin epoxy resin and the like, a hydrogenated bisphenol A epoxy resin, an aliphatic epoxy resin, a biphenyl-type epoxy resin and a dicyclo-type cyclic epoxy resin, which are a mainstream of a low water-absorption curing type, a naphthalene epoxy resin, polyfunctional epoxy resins such as trimethylolpropane polyglycidyl ether, glycerol polyglycidyl ether, pentaerythritol polyglycidyl ether and the like, fluorine-containing epoxy resins such as bisphenol AF epoxy resin and the like, a glycidyl(meth)acrylate, and others. These may be used singly or in a combination of two or more kinds.

The above publicly known epoxy resin may be solid or liquid at room temperature, but generally the epoxy resin preferably has an average epoxy equivalent of 100 to 2000. When the epoxy equivalent is 100 or more, a cured resin composition is not brittle and has suitable strength. On the other hand, when the epoxy equivalent is 2000 or less, the glass transition temperature (Tg) of the cured product is not low and thus suitable.

In a resin mixture of the above glycidyloxy-containing adamantane derivative and the above publicly known epoxy resin, the content of the glycidyloxy-containing adamantane derivative is preferably 5% by mass or more, and more preferably 10% by mass or more. When the content of the glycidyloxy-containing adamantane derivative is 5% by mass or more, optical characteristics, long-term heat resistance, and electric characteristics of a resin composition of the present invention become sufficient.

As a curing agent for an epoxy resin contained in a resin composition of the present invention, at least one kind selected from a cationic polymerization initiator, an acid anhydride type curing agent, an amine type curing agent, and a phenolic type curing agent and the like may be cited. In other words, a resin composition of the present invention may be cured by a cationic polymerization using a cationic polymerization initiator, by a reaction using a curing agent selected from an acid anhydride type curing agent, a phenolic type curing agent, an amine type curing agent and the like, or by a reaction using a cationic polymerization initiator and an acid anhydride curing agent. As far as the characteristics required of a cured product of the present invention (heat resistance and low water absorption) are not impaired, a curing agent other than these curing agents may be concurrently used as appropriate.

Any cationic polymerization initiator that reacts with an epoxy ring by heat or UV light may be used. Examples of such initiators include aromatic diazonium salts such as p-methoxybenzenediazonium hexafluorophosphate and the like; aromatic sulfonium salts such as triphenylsulfonium hexafluorophosphate and the like; aromatic iodonium salts such as diphenyliodonium hexafluorophosphate and the like; an aromatic iodosyl salt, an aromatic sulfoxonium salt, a metallocene compound and the like. Among them, aromatic sulfonium salts such as triphenylsulfonium hexafluorophosphate and the like, aromatic iodonium salts such as diphenyliodonium hexafluorophosphate and the like are most suitable. They may be used singly or in a combination of two or more kinds.

The use amount of the cationic polymerization initiator is preferably 0.01 to 5.0 parts by mass, more preferably 0.1 to 3.0 parts by mass relative to 100 parts by mass of the above glycidyloxy-containing adamantane derivative or the above resin mixture (hereinafter sometimes referred to as "Resin Component"). By choosing the content of the cationic polymerization initiator within the above range, suitable polymerization is achieved and good physical properties such as optical characteristics and the like may be expressed.

In a resin composition of the present invention, as the curing agent, an acid anhydride type curing agent, a phenolic type curing agent, an amine type curing agent and the like may be used in accordance with the purpose. By allowing an adamantane derivative of the present invention having excellent heat resistance and transparency to react with a curing agent, light resistance, dielectric constant and the like, in addition to heat resistance and transparency, may be improved, and solubility required for practical use may also be imparted.

Examples of the acid anhydride type curing agents include phthalic anhydride, maleic anhydride, trimellitic anhydride, pyromellitic anhydride, haxahydrophthalic anhydride, tetrahydrophthalic anhydride, methylnadic anhydride, nadic anhydride, glutaric anhydride, methylhexahydrophthalic anhydride, methyltetrahydrophthalic anhydride and the like. Among them, haxahydrophthalic anhydride, tetrahydrophthalic anhydride, methylhexahydrophthalic anhydride, and methyltetrahydrophthalic anhydride are most suitable. They may be used singly or in a combination of two or more kinds.

When an acid anhydride type curing agent is used, a curing accelerator may be blended in order to accelerate curing. Examples of such curing accelerators include a tertiary amine, an imidazole, an organic phosphine compound or a salt thereof, metallic soap such as zinc octylate, tin octylate and the like. They may be used singly or in a combination of two or more kinds.

Examples of the phenolic type curing agents include a phenol novolak resin, a cresol novolak resin, a bisphenol A novolak resin, a triazine-modified phenol novolak resin, a bisphenol, a polycondensate of a phenol (a phenol, an alkyl-substituted phenol, a naphthol, an alkyl-substituted naphthol, a dihydroxybenzene, a dihydroxynaphthalene and the like) with an aldehyde, a polymer of a phenol and a diene compound, a polycondensate of a phenol with an aromatic dimethylol, a polycondensate of bismethoxymethylbiphenyl with a naphthol or a phenol, a biphenol and a modified compound thereof, and the like.

Examples of the amine type curing agents include aromatic diamines such as m-phenylenediamine, 4,4'-diaminodiphenylmethane, 4,4'-diaminodiphenylsulfone, m-xylylenediamine, benzyldimethylamine and the like, diethylenetriamine, triethylenetetramine, isophorondiamine, dicyandiamide, tetraethylenepentamine, a ketimine compound, polyamide resin obtained by synthetic reaction of linoleinic acid dimer with ethylenediamine, and the like. They may be used singly or in a combination of two or more kinds.

Among these curing agents, an acid anhydride type curing agent and a phenolic type curing agent are preferable in view of physical properties of a cured resin such as transparency and the like, and particularly haxahydrophthalic anhydride, tetrahydrophthalic anhydride, methylhexahydrophthalic anhydride, and methyltetrahydrophthalic anhydride are most preferable.

Examples of other curing agents include an imidazole, a trifluoroboron-amine complex, a guanidine derivative and the like.

The blending ratio of a resin component and a curing agent is determined by the ratio of a glycidyloxy-reactive or epoxy-reactive functional group of the curing agent. The ratio is usually 0.2 to 1.5 equivalents, and preferably 0.5 to 1.3 equivalents of the functional group of the corresponding curing agent relative to one equivalent of a glycidyloxy or epoxy group. By choosing the blending ratio between the resin composition and the curing agent in the above range, there is no slowing of a curing rate of a resin composition or lowering of the glass transition temperature of a cured resin, or lowering of humidity resistance, either, thus it is suitable.

In a resin composition of the present invention, (C) a curing accelerator and (D) an inorganic filler may also be blended. As the above curing accelerator, there is no particular restriction, and examples thereof include diazabicycloalkenes such as 1,8-diazabicyclo[5.4.0]undecene-7 (DBU) and the like and salts thereof; tertiary amines such as triethylenediamine, tris(2,4,6-dimethylaminomethyl)phenol and the like and salts thereof; a primary amine and a secondary amine and salts thereof; a triazole and salts thereof; imidazoles such as 2-ethyl-4-methylimidazole, 2-methylimidazole and the like and salts thereof; phosphorous compounds such as triphenylphosphine (for example TTTP manufactured by Hokko Chemical Industry Co., Ltd.), tetraphenylphosphonium bromide, tetraphenylphosphonium-tetraphenylborate, tetra-n-butylphosphonium-o,o-diethylphosphorodithioate and the like; a quaternary ammonium salt, an organometallic salt, derivatives thereof, and the like. These may be used singly or concurrently. Among these curing accelerators, the use of a tertiary amine, an imidazole, and a phosphorous compound is preferable, and in view of storage stability and curing properties of a resin composition of the present invention, an imidazole and/or a tertiary amine are more preferable. In addition to the compound having a single chemical structure as mentioned above, fine particles which have a coated layer of a thermosetting resin on a nucleus of a compound having an imidazole skeleton (what is called a microcapsule) or amine adduct particles may be suitably used as the curing accelerators.

The content of the curing accelerator is preferably 0.01 to 8.0 parts by mass, more preferably 0.1 to 4.0 parts by mass, and further more preferably 1.0 to 4.0 parts by mass relative to 100 parts by mass of the above resin component. By choosing the content of the curing accelerator in the above range, sufficient curing accelerating effect may be obtained, and no coloring of a cured product is observed.

There is no particular restriction as to the inorganic filler designated as the (D) component. Examples of the inorganic fillers that may be used include glass powders, crystalline silica, fused silica, zinc oxide, alumina, fine silica powders, magnesia, titania, silicon nitride and the like. In a resin composition of the present invention for semiconductor sealing, fused silica is preferable and spherical fused silica is more preferable. The diameter of the inorganic filler may be selected appropriately in accordance with use, and is usually about several nanometers to about 10 p.m.

The blending amount of these inorganic fillers is usually about 30 to about 90% by mass and preferably 45 to 80% by mass relative to the total amount of a resin composition of the present invention. When the blending amount of the inorganic filler is 30% by mass or more, heat resistance is sufficiently improved and when 90% by mass or less decrease of fluidity or mechanical strength can be suppressed.

When a resin composition of the present invention is provided for the use requiring flame retardancy, a flame retardant may be blended as the (E) component as appropriate. There is no specific restriction as to the flame retardant, and it may be selected appropriately in accordance with use of a product thereof. For example, when applied to a product whose halogen does not cause problems, brominated epoxy resins such as a brominated phenol novolak epoxy resin, a brominated bisphenol A epoxy resin, and the like may be used. By blending these flame retardants, a resin composition having excellent solder-cracking resistance and humidity-resistant reliability may be obtained. The amount of these flame retardants is variable dependent on the blending ratio of the resin component, but usually about 0.5 to about 20% by mass as bromine content relative to the resin composition.

When applied to a product requiring halogen-free, phosphorous type flame retardants such as a phosphate ester, red phosphorus, 9,10-dihydro-9-oxa-10-phosphaphenanthlene-10-oxide (HCA), triarylphosphine oxide and the like, phosphagen, and others are preferable. The amount of these flame retardants is usually about 1 to about 15% by mass and preferably 3 to 12% by mass relative to the resin composition.

In a resin composition of the present invention, many kinds of publicly known additives that have been conventionally used may be blended as appropriate. Examples of such additives include a decay-preventing agent, a modifying agent, a silane coupling agent, a defoaming agent, a solvent, a leveling agent, an antioxidant, a mold-release agent, stress-releasing agents such as a silicone oil, a silicone resin and the like, a dye, a pigment, and others.

As a decay-preventing agent, such publicly known decay-preventing agents as a phenolic compound, an amine compound, an organic sulfur compound, a phosphorous compound and the like may be cited. By adding a decay-preventing agent, such properties as heat-resistance, transparency and the like of a cured product may be retained.

Examples of the phenolic compounds include commercially available materials such as Irganox 1010 (trademark, manufactured by Ciba Specialty Chemicals Inc.), Irganox 1076 (trademark, manufactured by Ciba Specialty Chemicals Inc.), Irganox 1330 (trademark, manufactured by Ciba Specialty Chemicals Inc.), Irganox 3114 (trademark, manufactured by Ciba Specialty Chemicals Inc.), Irganox 3125 (trademark, manufactured by Ciba Specialty Chemicals Inc.), Irganox 3790 (trademark, manufactured by Ciba Specialty Chemicals Inc.), BHT, Cyanox 1790 (trademark, Manufactured by Cyanamid Co.), Sumilizer GA-80 (trademark, manufactured by Sumitomo Chemical Co., Ltd.) and the like.

Examples of the amine compounds include compounds such as Irgastab FS042 (trademark, manufactured by Ciba Specialty Chemicals Inc.), GENOX EP (trademark, manufactured by Crompton Corporation, compound name: dialkyl-N-methylamine oxide) and the like; and hindered amines such as ADK STAB LA-52, LA-57, LA-62, LA-63, LA-67, LA-68, LA-77, LA-82, LA-87, and LA-94, all manufactured by Asahi Denka Co., Ltd., Tinuvin 123, 144, 440, 662, Chimassorb 2020, 119, and 944, all manufactured by Ciba Specialty Chemicals Inc., Hostavin N30 manufactured by Hoechst GmbH, Cyasorb UV-3346 and UV-3526, both manufactured by Cytec Industries Inc., Uval 299 manufactured by Great Lakes Chemical Corp., Sanduvor PR-31 manufactured by Clariant Corporation and the like.

Examples of the organic sulfur compounds include such commercially available products as DSTP (Yoshitomi) (trademark, manufactured by Yoshitomi Pharmaceutical Industries Ltd.), DLTP (Yoshitomi) (trademark, manufactured by Yoshitomi Pharmaceutical Industries Ltd.), DLTOIB (trademark, manufactured by Yoshitomi Pharmaceutical Industries Ltd.), DMTP (Yoshitomi) (trademark, manufactured by Yoshitomi Pharmaceutical Industries Ltd.), Seenox 412S (trademark, manufactured by SHIPRO KASEI KAISHA, LTD.), Cyanox 1212 (trademark, manufactured by Cyanamid Co.) and the like.

Examples of the modifying agents include publicly known modifying agents such as a glycol, a silicone, an alcohol and the like. Examples of the silane coupling agents include publicly known silane coupling agents such as a silane-type, a titanate-type and the like. Examples of the defoaming agents include publicly known defoaming agents such as a silicone type and the like. Examples of the solvents that may be used for resin powders or as a diluent solvent for coating include aromatic solvents such as toluene, xylene and the like, and ketone solvents such as MEK (methyl ethyl ketone), MIBK (methyl isobutyl ketone), cyclohexanone and the like, and others.

A resin composition of the present invention may be obtained by blending, for example, the above-mentioned resin component, a curing agent and/or a cationic polymerization initiator, and various additives, and, if necessary, they are further mixed, dispersed, and defoamed, by using a extruder, kneader, a roll, and the like (and they may be heated to appropriate temperature, if necessary) until homogeneity.

As a curing method for a resin composition of the present invention, there may be used, for example, a curing method in which a batch containing the above resin component, a curing agent and/or a cationic polymerization initiator, and various kinds of additives are mixed, formed to a target shape by charging into a mold (resin mold) or by coating, then cured by heating or irradiating a UV beam. In the case of thermal curing, curing temperature is usually about 50 to about 200° C., preferably 80 to 200° C., and more preferably 100 to 180° C. By choosing the temperature at 50° C. or above, poor curing does not occur, nor does coloring and the like at 200° C. or below. The curing time is dependent on a resin component, a curing agent, a curing accelerator, and an initiator to be used, but usually about 0.5 to about 10 hours and preferably 0.5 to 6 hours.

The irradiation strength of a UV beam is usually about 500 to about 5000 mJ/cm$^2$, and preferably 1000 to 4000 mJ/cm$^2$. Heating may be performed after the UV beam irradiation, preferably at 70 to 200° C. for 0.5 to 12 hours.

A molding method may be an injection molding, a blow molding, a press molding, a transfer molding and the like, and not particularly restricted, but the injection molding method in which a resin composition in pellet form is used in injection molding equipment may be preferably used.

A resin obtained by curing a resin composition of the present invention is excellent in heat resistance and transparency, and it is possible to attain 70% or more of total light transmittance. In addition, as will be shown in the later Examples, a cured resin product having excellent processability due to low melting point, high glass transition temperature, excellent durability (in heat resistance and light resistance), and good electric characteristics such as dielectric constant and the like can be obtained.

Accordingly, a resin composition of the present invention has excellent characteristics, thus is suitably used as a resin (a sealant and an adhesive) for an optical semiconductor (an LED and the like), a flat panel display (an organic EL device, a liquid crystal and the like), an electronic circuit, and an optical circuit (an optical waveguide); and optical electronic members such as a lens for optical communication, an optical film and the like.

Therefore, a resin composition of the present invention may be used also for a semiconductor element/an integrated circuit (an IC and the like), an individual semiconductor (a diode, a transistor, a thermistor and the like), an LED (an LED lamp, a chip LED, a light receiving element, and a lens for an optical semiconductor), a sensor (a temperature sensor, a light sensor, and a magnetic sensor), a passive component (a high frequency device, a resistor, a condenser and the like), a structural component (a connector, a switch, a relay and the like), an automobile part (a circuit system, a control system, sensors, a lamp seal and the like), an adhesive agent (for an optical component, an optical disk, a pickup lens) and the like, and, in addition, for an optical film and the like as surface coating.

Accordingly, the present invention also provides a sealing agent for an optical semiconductor, a sealing agent for electronic circuits such as an organic EL device and the like, an optical waveguide, optical electronic members such as a lens for optical communication, an optical film and the like, a semiconductor device, and a copper-clad laminate, made of the above-mentioned resin composition of the present invention.

A composition as a sealing agent for an optical semiconductor (LED and the like) may be applied to a bombshell type device or a surface mount type (SMT) device and the like, may adhere well with semiconductors such as GaN formed on a metal or a polyamide, and further may be used by dispersing fluorescent dyes such as YAG and the like in it. Furthermore, it may be used also for a surface coating material of a bombshell type LED and for a lens of a SMT type LED and the like.

A composition for an organic EL is applicable to the organic EL device having a composition of anode/hole-injection layer/luminescent layer/electron-injection layer/cathode, which is formed in this order on the transparent substrates such as generally used glasses, transparent resins and the like. As a sealing agent for an organic EL device, it may be used as an adhesive to cover an EL device by a resin film coated with a metal can, a metal sheet, or SiN and the like, or may directly seal an EL device by dispersing inorganic fillers and the like in order to impart a gas-barrier property to a resin composition of the present invention. It may be applied to a bottom emission type, which is currently a mainstream as a display system, but the effects of transparency and heat resistance of a resin composition of the present invention may be advantageously utilized when applied to a top emission type, which will draw attention in view of the light extraction efficiency and the like in the future.

A composition for an optical circuit is also applicable to a thermooptic switch and an arrayed waveguide grating for a single-mode and a multi-mode, an optical multiplexer/demultiplexer, a wavelength-variable filter, or a core material and a clad material for an optical fiber. It is also applicable to a micro lens array which focuses a light to a waveguide and a mirror of an MEMS-type optical switch. Further, it is applicable also to a dye binder and the like for a photoelectric transducer.

A composition for an optical film is applicable as a display of film substrates for liquid crystal, for organic EL and the like, or as a light diffusion film, an anti-reflection film, a color-converting film using dispersion of a fluorescent dye and the like.

A composition for an electronic circuit is applicable to an interlayer insulation film, an adhesive between a polyimide for a flexible print substrate and a copper foil, or a substrate resin. A copper-clad laminate may be prepared from a prepreg having glass cloth impregnated with the resin composition then dried and a copper foil.

A resin composition of the present invention may be used as a varnish by dissolving it in a solvent. There is no specific restriction as to the solvent as far as it can dissolve each component of the resin composition. Examples of such solvents include toluene, xylene, acetone, methyl ethyl ketone, methyl isobutyl ketone, dimethylformamide and the like. A copper-clad laminate of the present invention may be produced by impregnating the prepared varnish into such substrates as glass fibers, carbon fibers, polyester fibers, polyamide fibers, alumina fibers, paper and the like followed by heat-drying them to obtain a prepreg, which is then molded with a copper foil by a hot-press molding. The use amount of the above solvent is usually about 10 to about 70% by mass and preferably 15 to 65% by mass relative to the total of a resin composition of the present invention and the solvent.

A semiconductor device obtained by sealing a semiconductor device by a resin composition of the present invention and the above-mentioned copper-clad laminate have high heat resistance and low water absorption.

On the other hand, when permanent films such as an interlayer insulation film for a liquid crystal display, a protection film for a color filter, and the like are formed, a radiation-sensitive resin composition containing a sensitizer, an alkaline-soluble resin and the like is generally used. A glycidyloxy-containing adamantane derivative of the present invention is suitable as a crosslinking agent for the alkaline-soluble resin since it is excellent in heat resistance and transparency.

As a sensitizer, for example, an ester of a hydroxyl compound with a quinone diazido sulfonic acid may be used. Examples of the hydroxyl compounds include a polyvalent phenol-containing adamantane derivatives such as the adamantane derivatives represented by the above general formulas (II-1), (II-2), or (II-3), 2,3,4-trihydroxybenzophenone, 2,4,4'-trihydroroxybenzophenone, 2,3,4,4'-tetrahydroxybenzophenone, tris(4-hydroxyphenyl)methane, 1,1,2,2-tetrakis (4-hydroxyphenyl)ethane and the like. Among them, a polyvalent phenol-containing adamantane derivative is especially preferable in view of transparency.

There is no particular restriction as to the above alkaline-soluble resin, but polyvinylphenol, a novolak resin and the like may be mentioned as examples for it. One example of the novolak resin is a resin obtained by a conventional condensation reaction of an aldehyde with one or more kinds of phenols selected from phenol, o-cresol, m-cresol, p-cresol, 2,3-xylenol, 2,5-xylenol, 3,4-xylenol, 3,5-xylenol, 2,3,5-trimethylphenol, 3,4,5-trimethylphenol and the like.

Examples of the aldehydes include formaldehyde, trioxane, paraformaldehyde, acetaldehyde, benzaldehyde and the like. Among them, formaldehyde is preferably used.

A radiation-sensitive resin composition of the present invention may be prepared by dissolving, for instance, the above-mentioned sensitizer, an alkaline-soluble resin, and a glycidyloxy-containing adamantane derivative (a crosslinking agent) of the present invention into a solvent to give a solid concentration of about 20 to about 40% by mass and then filtering the solution through a filter having the pore diameter of about 0.2 μm.

Examples of the above solvents include methanol, ethanol, tetrahydrofuran, ethyleneglycol monomethyl ether, ethyleneglycol dimethyl ether, ethyleneglycol monoethyl ether, diethyleneglycol monomethyl ether, diethyleneglycol monoethyl ether, ethyleneglycol monoethyl ether acetate, propyleneglycol methyl ether acetate, propyleneglycol propyl ether acetate, ethyl acetate, butyl acetate, ethyl lactate, cyclohexanone, methyl ethyl ketone and the like.

A resist film may be formed by applying a radiation-sensitive resin composition of the present invention onto a silicon wafer, a glass substrate, a plastic substrate and the like by such coating methods as rotation coating, cast coating, roll coating and the like. As appropriate, the exposure is performed via a prescribed mask pattern after pre-baked. The prescribed pattern may be obtained by an alkaline development of the exposed resist film in an alkaline development solution.

A cured product obtained by curing a radiation-sensitive resin composition of the present invention is excellent in heat resistance and transparency, thus may be suitably used as permanent films such as an interlayer insulation film for a liquid crystal display, a protection film for a color filter and the like.

EXAMPLES

In the following, the present invention is explained in further detail, but the invention is not restricted at all by these Examples.

Example 1

Synthesis of 1-(2,4-diglycidyloxyphenyl)adamantane (the above formula (I-1))

(1) Synthesis of 1-(2,4-dihydroxyphenyl)adamantane

Into a four-neck flask having an inner volume of 500 ml and equipped with a reflux condenser, a stirrer, a thermometer, and a nitrogen inlet were charged 28.1 g (0.18 mol) of 1-adamantanol, 8.8 g (0.05 mol) of p-toluenesulfonic acid monohydrate, and 35 ml of ethanol. After the atmosphere was displaced by nitrogen, 39.6 g (0.36 mol) of resorcinol was added. The mixture in the flask was placed in an oil bath at 90° C. and heated and agitated for 3 hours. The reaction solution was cooled, added with 200 ml of pure water, agitated for 30 minutes, and then filtered to obtain a solid material. The material was dried under reduced pressure, then recrystallized from a methanol/toluene mixture solvent. The crystals obtained were collected with washing by toluene, and then dried under reduced pressure until constant weight to obtain the target compound (yield 86%).

This compound was identified by the nuclear magnetic resonance spectra ($^1$H-NMR and $^{13}$C-NMR). The measurements were done using DMSO-$d_6$ as a solvent by JNM-ECA500 manufactured by JEOL Ltd.

$^1$H-NMR (500 MHz): 1.66 (s, 6H), 2.01 (s, 9H), 6.14 (dd, 1H), 6.24 (d, 1H), 6.79 (d, 1H), 8.89 (s, 1H), 8.98 (s, 1H)

$^{13}$C-NMR (126 MHz): 28.47, 35.37, 36.68, 40.34, 103.61, 105.44, 126.32, 126.53, 155.79, 156.68

(2) Synthesis of 1-(2,4-diglycidyloxyphenyl)adamantane

Into a separable flask having an inner volume of 300 ml and equipped with a reflux condenser, a stiffer, a thermometer, and a nitrogen inlet were charged 30 ml of MIBK, 60 ml of DMSO, and 65 g (0.70 mol) of epichlorohydrin. After the atmosphere was displaced with nitrogen, 20.6 g (0.09 mol) of 1-(2,4-dihydroxyphenyl)adamantane synthesized in the above (1) was added and the mixture was heated to 45° C. with agitation. Into this solution, 7.6 g (0.19 mol) of sodium hydroxide was added over 0.5 hour, and the agitation was continued for another 0.5 hour. Then the temperature was raised to 65° C. and the agitation was continued for 2 hours. The reaction solution was cooled to room temperature, added with 25 ml of MIBK, and washed by water until the aqueous phase became neutral, and then the organic layer was concentrated to obtain yellowish viscous solution. The yellowish viscous solution was dissolved into 285 g of MEK, added with 3.4 g of 25% by mass of aqueous sodium hydroxide solution, and then heated under reflux with agitation for 2 hours. The solution was cooled to room temperature, washed with water until the aqueous phase became neutral from alkaline, and then the washing was done for two more times. The organic layer was concentrated to obtain the target compound (yield 94%). The LC (liquid chromatography) of this compound showed the purity of 95% (monomer content was 95% and the rests were oligomers of the target compound).

This compound was identified by the nuclear magnetic resonance spectra ($^1$H-NMR and $^{13}$C-NMR). The measurements were done using DMSO-$d_6$ as a solvent by JNM-ECA500 manufactured by JEOL Ltd.

$^1$H-NMR (500 MHz): 1.72 (s, 6H), 2.02 (s, 9H), 2.69 (dd, 1H), 2.76 (dd, 1H), 2.83 (dd, 1H), 2.87 (dd, 1H), 3.30 (m, 1H), 3.37 (m, 1H), 3.80 (dd, 1H), 3.87 (dd, 1H), 4.26 (dd, 1H), 4.32 (dd, 1H), 6.48 (dd, 1H), 6.56 (d, 1H), 7.02 (d, 1H)

$^{13}$C-NMR (126 MHz): 28.43, 35.80, 36.56, 40.42, 43.64, 43.71, 49.68, 49.77, 68.67, 68.86, 100.81, 105.26, 126.52, 130.51, 157.29, 158.02

Example 2

Synthesis of 1-(2,3,4-trihydroxyphenyl)adamantane (the above formula (II-1))

The target compound was obtained by performing the operation in the similar manner as Example 1 (1) except that resorcinol was changed to 45.3 g (0.36 mol) of pyrogallol in Example 1 (1) (yield 78%).

This compound was identified by the nuclear magnetic resonance spectra ($^1$H-NMR and $^{13}$C-NMR). The measurements were done using DMSO-$d_6$ as a solvent by JNM-ECA500 manufactured by JEOL Ltd.

$^1$H-NMR (500 MHz): 1.70 (s, 6H), 2.02 (s, 9H), 6.20 (d, 1H), 6.36 (d, 1H), 7.77 (br, 1H), 8.20 (br, 1H), 8.84 (br, 1H)

$^{13}$C-NMR (126 MHz): 28.46, 35.52, 36.68, 40.30, 105.49, 115.41, 127.27, 132.56, 143.84, 145.36

Example 3

Synthesis of 1-(2,3,4-triglycidyloxyphenyl)adamantane (the above formula (I-2))

The target compound was obtained by performing the operation in the similar manner as Example 1 (2) except that 1-(2,4-dihydroxyphenyl)adamantane was changed to 20.5 g of 1-(2,3,4-trihydroxyphenyl)adamantane synthesized in Example 2, and that the use amounts of epichlorohydrin and sodium hydroxide were changed to 80 g (0.86 mol) and 12.2 g (0.30 mol), respectively, in Example 1 (2) (yield 90%). The LC purity of this compound was 92% (monomer content was 92% and the rests were oligomers of the target compound).

This compound was identified by the nuclear magnetic resonance spectra ($^1$H-NMR and $^{13}$C-NMR). The measurements were done using DMSO-$d_6$ as a solvent by JNM-ECA500 manufactured by JEOL Ltd.

$^1$H-NMR (500 MHz): 1.76 (s, 6H), 2.04 (s, 9H), 2.68 (m, 3H), 2.85 (m, 3H), 3.36 (m, 3H), 3.84 (m, 3H), 4.28 (m, 3H), 6.53 (d, 1H), 6.68 (d, 1H)

$^{13}$C-NMR (126 MHz): 29.04, 36.82, 37.10, 41.24, 44.51, 44.60, 44.68, 50.68, 50.77, 50.86, 70.64, 70.73, 70.79, 105.39, 116.95, 121.20, 137.28, 146.34, 146.95

Example 4

Synthesis of 1,3-bis(2,4-dihydroxyphenyl)adamantane (the above formula (II-2))

Into a four-neck flask having an inner volume of 300 ml and equipped with a reflux condenser, a stirrer, a thermometer, and a nitrogen inlet were charged 16.0 g (0.10 mol) of 1,3-adamantanediol, 9.0 g (0.05 mol) of p-toluenesulfonic acid monohydrate, and 20 ml of 1,2-dimethoxyethane. After the atmosphere was displaced by nitrogen, 83.8 g (0.76 mol) of resorcinol was added. The mixture in the flask was placed in an oil bath at 90° C. and agitated for 6 hours. The mixture was cooled, added with 200 ml of pure water, agitated for 30 minutes, and then filtered to obtain a solid material. The material was dried under reduced pressure, then recrystallized from a methanol/water mixture solution. The crystals obtained were collected with washing by toluene, and then dried under reduced pressure until constant weight to obtain the target compound (yield 85%).

This compound was identified by the nuclear magnetic resonance spectra ($^1$H-NMR and $^{13}$C-NMR). The measurements were done using DMSO-$d_6$ as a solvent by JNM-ECA500 manufactured by JEOL Ltd.

$^1$H-NMR (500 MHz): 1.64 (s, 2H), 1.94 (m, 8H), 2.09 (s, 2H), 2.23 (s, 2H), 6.10 (dd, 2H), 6.20 (d, 2H), 6.81 (d, 2H), 8.86 (s, 2H), 8.92 (s, 2H)

$^{13}$C-NMR (126 MHz): 29.17, 36.23, 36.34, 39.88, 43.44, 103.59, 105.43, 126.39, 126.64, 155.71, 156.68

Example 5

Synthesis of 1,3-bis(2,4-diglycidyloxyphenyl)adamantane (the above formula (I-3))

The target compound was obtained by performing the operation in the similar manner as Example 1 (2) except that 1-(2,4-dihydroxyphenyl)adamantane was changed to 20.5 g (0.06 mol) of 1,3-bis(2,4-dihydroxyphenyl)adamantane synthesized in Example 4, and that the use amounts of epichlorohydrin and sodium hydroxide were changed to 80 g (0.86 mol) and 12.2 g (0.30 mol), respectively, in Example 1 (2) (yield 72%). The LC purity of this compound was 88% (monomer content was 88% and the rests were oligomers of the target compound).

This compound was identified by the nuclear magnetic resonance spectra ($^1$H-NMR and $^{13}$C-NMR). The measurements were done using DMSO-$d_6$ as a solvent by JNM-ECA500 manufactured by JEOL Ltd.

$^1$H-NMR (500 MHz): 1.73 (s, 2H), 1.98 (br, 4H), 2.11 (br, 6H), 2.30 (s, 2H), 2.70 (m, 4H), 2.82 (m, 4H), 3.31 (m, 4H), 3.84 (m, 4H), 4.29 (m, 4H), 6.49 (dd, 2H), 6.60 (d, 2H), 7.08 (d, 2H)

$^{13}$C-NMR (126 MHz): 29.71, 36.48, 37.44, 40.40, 44.20, 44.30, 44.68, 50.29, 50.35, 69.28, 69.46, 101.50, 105.95, 127.20, 131.10, 157.88, 158.67

Example 6

Synthesis of
1,3-bis(2,3,4-trihydroxyphenyl)adamantane (the above formula (II-3))

The target compound was obtained by performing the operation in the similar manner as Example 4 except that resorcinol was changed to 96.0 g (0.76 mol) of pyrogallol in Example 4 (yield 83%).

This compound was identified by the nuclear magnetic resonance spectra ($^1$H-NMR and $^{13}$C-NMR). The measurements were done using acetone-$d_6$ as a solvent by JNM-ECA500 manufactured by JEOL Ltd.

$^1$H-NMR (500 MHz): 1.79 (s, 2H), 2.15 (s, 8H), 2.19 (s, 2H), 2.46 (s, 2H), 6.32 (d, 2H), 6.56 (d, 2H), 6.92 (br, 2H), 7.37 (br, 2H), 7.99 (br, 2H)

$^{13}$C-NMR (126 MHz): 30.83, 37.42, 37.95, 41.07, 44.78, 106.68, 117.23, 129.13, 133.30, 144.18, 146.08

Example 7

Synthesis of
1,3-bis(2,3,4-triglycidyloxyphenyl)adamantane (the above formula (I-4))

The target compound was obtained by performing the operation in the similar manner as Example 1 (2) except that 1-(2,4-dihydroxyphenyl)adamantane was changed to 20.5 g (0.05 mol) of 1,3-bis(2,3,4-trihydroxyphenyl)adamantane synthesized in Example 6, and that the use amounts of epichlorohydrin and sodium hydroxide were changed to 80 g (0.86 mol) and 14.4 g (0.36 mol), respectively in Example 1 (2) (yield 66%). The LC purity of this compound was 83% (monomer content was 83% and the rests were oligomers of the target compound).

This compound was identified by the nuclear magnetic resonance spectra ($^1$H-NMR and $^{13}$C-NMR). The measurements were done using DMSO-$d_6$ as a solvent by JNM-ECA500 manufactured by JEOL Ltd.

$^1$H-NMR (500 MHz): 1.73 (s, 2H), 2.01 (br, 4H), 2.15 (br, 6H), 2.32 (s, 2H), 2.68 (m, 6H), 2.81 (m, 6H), 3.35 (m, 6H), 3.79 (m, 6H), 4.33 (m, 6H), 6.35 (d, 2H), 6.65 (d, 2H)

$^{13}$C-NMR (126 MHz): 29.78, 36.53, 37.64, 40.39, 44.20, 44.41, 44.51, 44.68, 50.27, 50.34, 50.46, 69.18, 69.30, 69.42, 106.31, 119.40, 121.20, 135.95, 146.21, 146.88

Example 8

Synthesis of
2,2-bis(2,4-dihydroxyphenyl)adamantane (the above formula (II-4))

Into a four-neck flask having an inner volume of 3000 ml and equipped with a reflux condenser, a stirrer, a thermometer, and a nitrogen inlet were charged 50 g (0.33 mol) of 2-adamantanone, 176 g (1.60 mol) of resorcinol, 50 ml of hydrochloric acid, and 14 g (0.13 mol) of 3-mercaptopropionic acid. After the atmosphere was displaced by nitrogen, the mixture in the flask was placed in an oil bath at 80° C. and heated and agitated for 6 hours. The mixture was added with 150 ml of pure water, cooled to room temperature, then added with 360 g of 10% by mass of sodium hydroxide aqueous solution to precipitate a solid material. The material was collected by filtration with washing by pure water, dried under reduced pressure, then recrystallized from a methanol/water mixture solution. The crystals obtained were collected with washing by toluene, and then dried under reduced pressure until constant weight to obtain the target compound (yield 34%).

This compound was identified by the nuclear magnetic resonance spectra ($^1$H-NMR and $^{13}$C-NMR). The measurements were done using DMSO-$d_6$ as a solvent by JNM-ECA500 manufactured by JEOL Ltd.

$^1$H-NMR (500 MHz): 1.70-1.77 (m, 8H), 2.01 (d, 4H), 3.12 (s, 2H), 2.32 (s, 2H), 6.12 (dd, 2H), 6.21 (d, 2H), 6.80 (d, 2H), 8.87 (s, 2H), 8.95 (s, 2H)

$^{13}$C-NMR (126 MHz): 27.41, 32.13, 33.44, 38.12, 49.19, 103.74, 105.54, 126.61, 126.83, 155.22, 155.94

Example 9

Synthesis of
2,2-bis(2,4-diglycidyloxyphenyl)adamantane (the above formula (I-5))

The target compound was obtained by performing the operation in the similar manner as Example 1 (2) except that 1-(2,4-dihydroxyphenyl)adamantane was changed to 20.5 g (0.06 mol) of 2,2-bis(2,4-dihydroxyphenyl)adamantane synthesized in Example 8, and that the use amounts of epichlorohydrin and sodium hydroxide were changed to 80 g (0.86 mol) and 12.2 g (0.30 mol), respectively, in Example 1 (2) (yield 66%). The LC purity of this compound was 88% (monomer content was 88% and the rests were oligomers of the target compound).

This compound was identified by the nuclear magnetic resonance spectra ($^1$H-NMR and $^{13}$C-NMR). The measurements were done using DMSO-$d_6$ as a solvent by JNM-ECA500 manufactured by JEOL Ltd.

$^1$H-NMR (500 MHz): 1.69-1.79 (m, 8H), 2.02 (d, 4H), 2.68 (m, 4H), 2.81 (m, 4H), 3.15 (s, 2H), 3.28 (m, 4H), 3.81 (m, 4H), 4.26 (m, 4H), 6.59 (d, 2H), 6.50 (dd, 2H), 7.02 (d, 2H)

$^{13}$C-NMR (126 MHz): 27.22, 32.21, 33.53, 38.03, 44.60, 44.75, 44.68, 49.39, 50.13, 50.20, 68.61, 68.70, 101.70, 105.81, 126.74, 130.95, 156.92, 157.86

Example 10

A batch containing 1 g of 1-(2,4-diglycidyloxyphenyl)adamantane obtained by the synthesis in Example 1 (2), 0.88 g of methylhexahydrophthalic anhydride (trade name MH700, manufactured by New Japan Chemical Co., Ltd.) as an acid anhydride, and 0.01 g of 1,8-diazabicyclo[5.4.0]undecene-7 (trade name SA102, manufactured by San-Apro Limited) as a curing accelerator was blended at room temperature and defoamed to obtain a resin composition, which was then heated at 120° C. for 2 hours and at 150° C. for 2 hours to prepare a cured resin (a sheet of 3 mm thickness). The glass transition temperature and the light transmittance of the cured resin product thus obtained were measured, and then it was further subjected to the tests for light resistance and long-term heat resistance in the way as following. The evaluation results are shown in Table 1.
(1) Glass Transition Temperature By using a differential scanning calorimeter (DSC-7, manufactured by PerkinElmer, Inc.), 10 mg of a sample was kept at 50° C. for 5 minutes under nitrogen atmosphere and then heated at 10° C./min. A discontinuous point observed in the thermal flux curve thereby obtained was taken as a glass transition temperature Tg.

(2) Light Transmittance

A 3 mm-thick specimen of a sample was measured in accordance with the procedure in JIS K7105 at the measured wavelength of 400 nm (unit %). A spectrophotometer UV-3100S, manufactured by Shimadzu Corporation, was used as the measuring instrument.

(3) Light Resistance Test

By using Suntest CPS+, manufactured by Toyo Seiki Seisaku-Sho, Ltd., a sample was irradiated at 60° C. by light for 500 hours, and the change of the light transmittance at 400 nm before and after the irradiation was measured by using a sunshine tester. When the transmittance was decreased by less than 20%, it was rated as "○", and when decreased by 20% or more, it was rated as "X".

(4) Long-Term Heat Resistance Test

The change of the light transmittance at 400 nm of a sample before and after it was kept in an oven controlled at 140° C. for 100 hours was measured by a sunshine tester. After keeping it in the oven, when the transmittance was decreased by less than 20%, it was rated as "○", and when decreased by 20% or more, it was rated as "X".

Example 11

A cured resin product was prepared and evaluated in the similar manner as Example 10 except that 1-(2,4-diglycidyloxyphenyl)adamantane in Example 10 was changed to 1-(2,3,4-triglycidyloxyphenyl)admantane obtained by the synthesis in Example 3 and that the use amount of methylhexahydrophthalic anhydride was changed to 1.08 g. The evaluation results are shown in Table 1.

Example 12

A cured resin product was prepared and evaluated in the similar manner as Example 10 except that 1-(2,4-diglycidyloxyphenyl)adamantane in Example 10 was changed to 1,3-bis(2,3,4-glycidyloxyphenyl)admantane obtained by the synthesis in Example 5 and that the use amount of methylhexahydrophthalic anhydride was changed to 1.02 g. The evaluation results are shown in Table 1.

Example 13

A cured resin product was prepared and evaluated in the similar manner as Example 10 except that 1-(2,4-diglycidyloxyphenyl)adamantane in Example 10 was changed to 1,3-bis(2,3,4-triglycidyloxyphenyl)admantane obtained by the synthesis in Example 7 and that the use amount of methylhexahydrophthalic anhydride was changed to 1.17 g. The evaluation results are shown in Table 1.

Example 14

A cured resin was prepared and evaluated in the similar manner as Example 10 except that 1-(2,4-diglycidyloxyphenyl)adamantane in Example 10 was changed to 2,2-bis(2,4-diglycidyloxyphenyl)admantane obtained by the synthesis in Example 9 and that the use amount of methylhexahydrophthalic anhydride was changed to 1.02 g. The evaluation results are shown in Table 1.

Comparative Example 1

A cured resin product was prepared and evaluated in the similar manner as Example 10 except that 1-(2,4-diglycidyloxyphenyl)adamantane in Example 10 was changed to bisphenol A epoxy resin (trade name Epikote 828, manufactured by Japan Epoxy Resins Co., Ltd.) and that the use amount of methylhexahydrophthalic anhydride was changed to 0.91 g. The evaluation results are shown in Table 1.

TABLE 1

|  | Example 10 | Example 11 | Example 12 | Example 13 | Example 14 | Comparative Example 1 |
|---|---|---|---|---|---|---|
| Glass transition temp. (° C.) | 165 | 171 | 206 | 183 | 215 | 130 |
| Light transmittance (%) | 91 | 91 | 89 | 88 | 89 | 80 |
| Light resistance test | ○ | ○ | ○ | ○ | ○ | X |
| Heat resistance test | ○ | ○ | ○ | ○ | ○ | ○ |

Example 15

A batch containing 100 parts by mass of 1-(2,4-diglycidyloxyphenyl)adamantane, 89.2 parts by mass of methylhexahydrophthalic anhydride (trade name MH700, manufactured by New Japan Chemical Co., Ltd.) as a curing agent, 2 parts by mass of 2,4,6-tris(dimethylaminomethyl)phenol (trade name TAP, manufactured by Kayaku Akzo COrporation) as a curing accelerator, 191.7 parts by mass of spherical fused silica (trade name FB-7SDC, manufactured by Denki Kagaku Kogyo Kabushiki Kaisha) as an inorganic filler, and 0.5 part by mass of carbon black (trade name #3030B, manufactured by Mitsubishi Chemical Corporation) as a color pigment was kneaded at 100° C. for 8 minutes by a hot roll, and thereafter press-molded at 3 MPa and 170° C. for 120 seconds. It was then cured at 170° C. for 5 hours to obtain an article having the size of 10 mm×10 mm×2 mm. The solder resistance, the water absorption and the like of the article obtained were measured in the following way. The evaluation results are shown in Table 2.

(1) Solder Resistance

After five of the above-mentioned articles were subjected to the moisturization treatment at 85° C. and 85% of relative humidity for 48 hours, they were immersed in a Pb-free soldering bath at 300° C. for 30 seconds to observe whether formation of cracks occurs or not on their surfaces.

(2) Water Absorption

After ten of the above-mentioned articles were subjected to the moisturization treatment at 85° C. and 85% of relative humidity for 48 hours, the water absorption was calculated by the following equation based on the weight increase.

Water absorption(%)=(weight increase/dry weight)×100

(3) Glass Transition Temperature (Tg)

This was measured in the same manner as before.

Examples 16, 17, and Comparative Examples 2 and 3

Articles were obtained and evaluated in the similar manner as Example 15 by using the following substances in the blend with their amounts (parts by mass) being shown in Table 2. The evaluation results are shown in Table 2.

Epoxy resin 1: 1-(2,4-digylcidyloxyphenyl)adamantane (synthesized in Example 1 (1))
Epoxy resin 2: 1,3-bis(2,4-diglycidyloxyphenyl)adamantane (synthesized in Example 5)
Epoxy resin 3: bisphenol A epoxy resin (trade name Epikote 828, manufactured by Japan Epoxy Resins Co., Ltd.)
Epoxy resin 4: 3,4-epoxycyclohexylmethyl(3,4-epoxy)cyclohexylcarboxylate (trade name Celloxide 2021P, manufactured by Daicel Chemical Industries, Ltd.)
Curing agent 1: methylhexahydrophthalic anhydride (trade name MH700, manufactured by New Japan Chemical Co., Ltd.)
Curing agent 2: phenolic resin (trade name YLH903, manufactured by Japan Epoxy Resins Co., Ltd.)
Curing accelerator: 2,4,6-tris(dimethylaminomethyl)phenol (trade name TAP, manufactured by Kayaku Akzo Corporation)
Inorganic filler: spherical fused silica (trade name FB-7SDC, manufactured by Denki Kagaku Kogyo Kabushiki Kaisha, average particle size 7 μm)
Color pigment: carbon black (trade name #3030B, manufactured by Mitsubishi Chemical Corporation)

TABLE 2

| | Example 15 | Example 16 | Example 17 | Comparative Example 2 | Comparative Example 3 |
|---|---|---|---|---|---|
| Epoxy resin 1 | 100 | 100 | 80 | | |
| Epoxy resin 2 | | | 20 | | |
| Epoxy resin 3 | | | | 100 | |
| Epoxy resin 4 | | | | | 100 |
| Curing agent 1 | 89.2 | | 92.0 | 87.3 | 123.1 |
| Curing agent 2 | | 91.9 | | | |
| Curing accelerator | 2.0 | 1.5 | 2.0 | 2.0 | 2.0 |
| Inorganic filler | 191.7 | 193.9 | 194.5 | 189.8 | 225.6 |
| Color pigment | 0.5 | 0.5 | 0.5 | 0.5 | 0.5 |
| Water absorption (% by mass) | 0.55 | 0.53 | 0.65 | 0.58 | 1.10 |
| Glass transition temperature (° C.) | 190 | 225 | 213 | 149 | 210 |
| Solder resistance (number of NG/total number) | 0/5 | 0/5 | 0/5 | 1/5 | 4/5 |

Example 18 and Comparable Example 4

A batch comprising the components as shown in Table 3 was dissolved in methyl ethyl ketone solvent (MEK) to prepare a varnish having solid component concentration of 60% by mass. Glass cloth (trade name 7628, manufactured by Nitto Boseki Co., Ltd.) was impregnated with the varnish, dried by air, and heated at 150° C. for 2 minutes to remove MEK to obtain prepregs. Eight of the prepregs were stacked, and pressed for curing with a copper foil (trade name JTC, thickness of 35 μm, manufactured by Nikko Materials Co., Ltd.) on one side of the stack at 200° C. and 4.5 MPa for 2 hours to obtain a copper-clad laminate. Five cupper-clad laminates thus obtained were subjected to moisturization at 85° C. and 85% of relative humidity for 48 hours, immersed in a Pb-free soldering bath at 300° C. for 30 seconds, and then it was examined whether or not the blistering takes place at the copper foil part. Water absorption and glass transition temperature were measured in the same way as mentioned above. The evaluation results are shown in Table 3.

It should be noted that epoxy resins 1 and 4, curing agent 2, a curing accelerator, and a color pigment in Table 3 were the same as those described in Table 2. In Table 3, the flame retardant was brominated epoxy resin (trade name BROC, bromine content of 49% by mass, epoxy equivalent of 340, manufactured by Nippon Kayaku Co., Ltd.), and the flame retardant adjuvant agent was antimony trioxide (trade name PATOX-HS, manufactured by Nihon Seiko Co., Ltd.).

TABLE 3

| | Example 18 | Comparative Example 4 |
|---|---|---|
| Epoxy resin 1 | 65.0 | |
| Epoxy resin 4 | | 60.0 |
| Flame retardant | 35.0 | 40.0 |
| Curing agent 2 | 77.2 | 96.1 |
| Curing accelerator | 1.5 | 1.5 |
| Inorganic filler | 183.7 | 203.1 |
| Flame retardant adjuvant agent | 4.5 | 5.0 |
| Color pigment | 0.5 | 0.5 |
| Water absorption (% by mass) | 0.8 | 1.42 |
| Glass transition temperature (° C.) | 175 | 201 |
| Solder resistance (number of NG/total number) | 0/5 | 5/5 |

Preparation Example 1

Into a four-neck flask having an inner volume of 300 ml and equipped with a reflux condenser, a stirrer, a thermometer, and a nitrogen inlet were charged 10 g (0.04 mol) of 1-(2,3,4-trihydroxyphenyl)adamantane obtained by the synthesis in Example 2 and 41 g (0.15 mol) of 2-diazo-1,2-naphthoquinone-5-sulfonyl chloride, and they were dissolved in 100 ml of acetone. Then 19 g (0.19 mol) of triethylamine was slowly added so that the reaction temperature might not exceed 25° C., and then the agitation was continued for another 2 hours. The formed salt was removed by filtration, the reaction mixture solution was poured into 1 liter of pure water, and then deposited solids were collected by filtration, washed by water, and dried to obtain quinone diazidosulfonate ester of 1-(2,3,4-trihydroxyphenyl)adamantane (yield 46%).

Preparation Example 2

Quinone diazidosulfonate ester of 1,3-bis(2,4-dihydroxyphenyl)adamantane was obtained in the similar manner as Preparation Example 1 except that 1-(2,3,4-trihydroxyphenyl)adamantane in Preparation Example 1 was changed to 10 g (0.03 mol) of 1,3-bis(2,4-dihydroxyphenyl)adamantane obtained by the synthesis in Example 4 (yield 38%).

Preparation Example 3

Quinone diazidosulfonate ester of 1,3-bis(2,3,4-trihydroxyphenyl)adamantane was obtained in the similar manner as Preparation Example 1 except that 1-(2,3,4-trihydroxyphenyl)adamantane in Preparation Example 1 was changed to 8 g (0.02 mol) of 1,3-bis(2,3,4-trihydroxyphenyl)adamantane obtained by the synthesis in Example 6 (yield 29%).

Example 19

A mixture of 100 parts by mass of phenol novolak resin (trade name Sumilite Resin, manufactured by Sumitomo Bakelite Co., Ltd.), 20 parts by mass of the quinone diazidosulfonate ester obtained in Preparation Example 1 as a sensitizer, and 10 parts by mass of 1-(2,4-diglycidyloxyphenyl)adamantane obtained in Example 1 (2) as a crosslinking agent was dissolved into ethyl lactate to give 20% by mass of the solid component concentration. This solution was filtrated through a filter having 0.2 μm of pore diameter to obtain a radiation-sensitive resin composition.

Example 20

A radiation-sensitive resin composition was obtained in the similar manner as Example 19 except that the quinone diazidosulfonate ester compound obtained in Preparation Example 1 was changed to the quinone diazidosulfonate ester compound obtained in Preparation Example 2.

Example 21

A radiation-sensitive resin composition was obtained in the similar manner as Example 19 except that the quinone diazidosulfonate ester compound obtained in Preparation Example 1 was changed to the quinone diazidosulfonate ester compound obtained in Preparation Example 3.

Comparative Example 5

A radiation-sensitive resin composition was obtained in the similar manner as Example 19 except that 1-(2,4-diglycidyloxyphenyl)adamantane obtained in Example 1 (2) as a crosslinking agent was changed to the bisphenol A epoxy resin.

Test Example 1

The radiation-sensitive resin compositions obtained as above were applied on a silicon wafer by a spin coating method so that the dry thickness of film might be 1.05 μm, and then dried on a hot plate controlled at 110° C. for 90 seconds to obtain a photoresist film. The photoresist film was exposed by an i-ray and developed by using 2.38% by mass of aqueous solution of hydroxylated tetramethyl ammonium at 23° C. for 60 seconds. The sensitivity curve was prepared, and by referring to it the sensitivity and the film remaining rate of the radiation-sensitive resin composition were obtained. The results are shown in Table 4.

TABLE 4

|  | Example 19 | Example 20 | Example 21 | Comparative Example 5 |
|---|---|---|---|---|
| Sensitivity (mJ/cm$^2$) | 38 | 37 | 35 | 45 |
| Film remaining rate (%) | 99 | 99 | 99 | 93 |

INDUSTRIAL APPLICABILITY

A resin composition containing an adamantane derivative of the present invention gives a cured product having excellent optical characteristics such as transparency, light resistance and the like, heat resistance, electric characteristics such as dielectric constant and the like, and low water absorption, and can be suitably used as a sealing agent for an electronic circuit (a sealing agent for an optical semiconductor, an organic EL device and the like), as an optical electronic member (an optical waveguide, an optical communication lens, an optical film and the like) and an adhesive agent for them, and also as a sealing agent for a semiconductor, a copper-clad laminate, a crosslinking agent for a radiation-sensitive resin composition, and others. In addition, an adamantane derivative of the present invention is useful as a crosslinking agent for a radiation-sensitive resin composition for a liquid crystal display and the like, because of its excellent heat resistance and transparency.

The invention claimed is:

1. An adamantane compound represented by the following general formula (I-1),

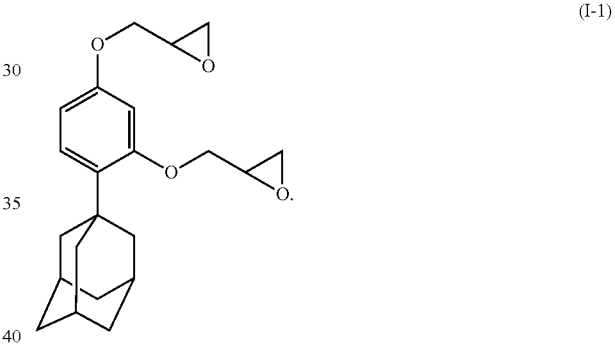

2. An adamantane compound represented by the following general formula (I-3),

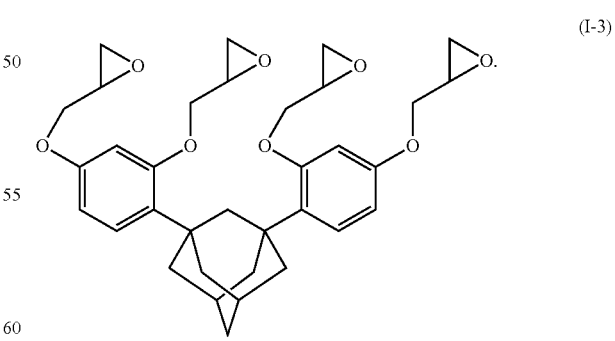

3. A method of producing an adamantane compound according to claim 1, said method comprising allowing an adamantane compound represented by the following general formula (II) to react with epichlorohydrin,

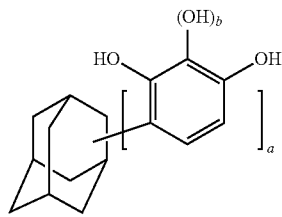 (II)

wherein in the formula, a is 1, and b is 0.

4. A resin composition comprising (A) a resin comprising the adamantane compound according to claim 1 and (B) an epoxy resin curing agent.

5. The resin composition according to claim 4, wherein (B) the epoxy resin curing agent is one or more selected from the group consisting of a cationic polymerization initiator, an acid anhydride compound, and a phenolic resin.

6. The resin composition according to claim 4, further comprising (C) a curing accelerator and (D) an inorganic filler.

7. The resin composition according to claim 6, further comprising (E) a flame retardant.

8. A radiation-sensitive resin composition comprising the adamantane compound according to claim 1 as a crosslinking agent.

9. An optical electronic member comprising the adamantane compound according to claim 1.

10. A sealing agent for an electronic circuit comprising the adamantane compound according to claim 1.

11. A semiconductor device wherein a semiconductor element is sealed with the resin composition according to claim 4.

12. A copper-clad laminate comprising the resin composition according to claim 4.

13. The adamantine compound according to claim 2 having a glass transition temperature of 219° C.

* * * * *